United States Patent [19]

Lambert et al.

[11] Patent Number: 4,859,607
[45] Date of Patent: Aug. 22, 1989

[54] COLORIMETRIC DETECTOR FOR OZONE AND METHOD OF PREPARATION

[75] Inventors: Jack L. Lambert, Manhattan; Yuan C. Chiang, Salina; Joseph V. Paukstelis, Manhattan, all of Kans.

[73] Assignee: Kansas State University Research Foundation, Manhattan, Kans.

[21] Appl. No.: 297,960

[22] Filed: Jan. 17, 1989

[51] Int. Cl.$^4$ .............................................. G01N 33/00
[52] U.S. Cl. .................................. 426/135; 427/384; 427/395; 436/166
[58] Field of Search ................ 436/135, 166; 427/384, 427/395

[56] References Cited

U.S. PATENT DOCUMENTS

| | | | |
|---|---|---|---|
| 3,397,966 | 8/1968 | Plantz | 436/135 |
| 4,260,679 | 4/1981 | Tsudal et al. | 436/135 |
| 4,820,632 | 4/1989 | Frey et al. | 436/135 |

OTHER PUBLICATIONS

Lambert, J. L.; Paukstells, J. V.; "3–Methyl–2–benzothiazolinone Acetone Azine with 2–Phenylphenol as a Solid Passive Monitoring Reagent for Ozone", Environ. Sci. Technol., 1989, vol. 23, No. 2, pp. 241–243.

*Primary Examiner*—Barry S. Richman
*Assistant Examiner*—Marcella Iris Fruchter
*Attorney, Agent, or Firm*—Tilton, Fallon, Lungmus & Chestnut

[57] ABSTRACT

3-Methyl-2-benzothiazolinone acetone azine and 2-phenylphenol in 1:4 molar solid mixture reacts specifically with ozone at concentrations of environmental interest to produce a red-violet color. The response is proportional, but not rectilinearly, to ozone concentration at constant exposure time and to time of exposure at constant ozone concentration. The reagent is intended for use with visual comparison standards in passive monitoring devices. No interference was observed from atmospheric oxygen, nitrogen dioxide, sulfur dioxide, or bromine or iodine vapor. Chlorine produced a light yellow color.

12 Claims, No Drawings

COLORIMETRIC DETECTOR FOR OZONE AND METHOD OF PREPARATION

FIELD OF INVENTION

The field of this invention is colorimetric detectors for strong atmospheric oxidants, particularly ozone and carbon dioxide.

GRANT REFERENCE

This invention resulted in part from research carried out under National Science Foundation grant No. CHE-8311-011.

BACKGROUND OF INVENTION

Prior research efforts have been directed to the discovery of reagents or detector systems for use in passive monitoring devices that are specific either for ozone or nitrogen dioxide. Tin(II)-di-phenylcarbazide solid reagent which has been found to be responsive to both ozone and nitrogen dioxide; Lambert, et al., *C. Anal. Latt.*, 1981, 14, 663; and Lambert, et al., *Anal. Chem.*, 1982, 54, 1227. More recently it was discovered that phenoxazine can be used as a solid monitoring agent for ozone and/or nitrogen dioxide; Lambert, et al., *Environ. Sci. Technol.*, 1987, 21, 503. Phenoxazine reacts to both ozone and nitrogen dioxide but the colors produced are distinctive, a dull brown being formed with ozone and a red-orange with nitrogen dioxide. The search has continued for better and more specific colorimetric detectors for ozone.

SUMMARY OF INVENTION

This invention is based on the discovery that 3-methyl-2-benzothiazolinone (MBTH) can be reacted with ketones to form one part of a reagent system for detection of ozone. For example, the first component of the system may be MBTH acetone azine. The second component of the solid phase detection system is a hydroxyphenyl compound which contains at least one phenyl group with a hydroxy substituent. Preferably the phenyl group is unsubstituted in the ortho or para position, or unsubstituted in both the ortho and para positions with reference to the hydroxy substituent.

Using the reagent system of this invention, a solution is formed of the two reagents in an inert organic solvent, which is applied to an inert solid support. The applied solution is evaporated to form a solid phase mixture of the two reagents on the support for use as the colorimetric detector.

MBTH hydrazone hydrochloride is a known compound which has been used in colorimetric determination of aromatic amines and amino heteroaromatic compounds. It has been reported as particularly useful for determination of aldehydes such as formaldehyde in auto exhaust fumes or polluted air. See Sawicki, et al., *Anal. Chem.*, 33, 722; and Fieser and Fieser, "Reagents for Organic Synthesis", John Wiley and Sons, New York, 1967, MBTH is not known to have been used in any form or in combination with any other reagent for colorimetric determination of oxidizing agents such as ozone or nitrogen dioxide.

Some embodiments of the invention provide a reagent system which is sensitive to both ozone and nitrogen dioxide. However, in the preferred embodiments the system is sensitive only to ozone, and nitrogen dioxide does not produce a color reaction. For example, such as preferred combination of reagents is MBTH acetone azine and 2-phenylphenol. When an intimate mixture of these reagents is exposed to ozone at parts per million concentrations, a distinctive red-violet color is produced, the intensity of which increases with the concentration of the ozone. There is substantially no color reaction with nitrogen dioxide at similar concentrations, nor with other atmospheric oxidizing agents such as sulfur dioxide, bromine vapor, or iodine vapor. The nature of the color reaction has not been determined, but it appears to involve the formation of a novel chromogen.

DETAILED DESCRIPTION

One of the reagents for use in the detection system of this invention is a 3-methyl-2-benzothiazolinone (MBTH) ketone azine. As subsequently illustrated herein, the MBTH ketone azines can be prepared from MBTH hydrazone hydrochloride which is commercially available. Alternatively, MBTH hydrazone hydrochloride can be prepared according to the method of Sawicki, et al., *Anal. Chem.*, 1961, 33, 93.

To prepare the reagent of this invention, any ketone reactable with MBTH as a free base or with MBTH hydrazone can be employed. The ketone may be aliphatic, cyclic, or aromatic. It should contain at least one ketone group. The lower aliphatic ketones ($C_2$ to $C_4$) are preferred, such as acetone or methylethyl ketone. However, other MBTH reactable ketones can be used, such as cyclohexanone or phenylcyclohexanone. A specifically preferred reagent is 3-methyl-2-benzothiazolinone acetone azine.

The MBTH ketone azine is employed in combination with a hydroxyphenyl compound. To provide a color reaction with ozone or in some embodiments with both ozone and nitrogen dioxide, the molecular configuration of the hydroxyphenyl compound is believed to be of importance. Broadly stated, the preferred class of hydroxyphenyl compounds is compounds which contain at least one phenyl group having a hydroxy substituent and which is unsubstituted in the ortho or para positions, or in both the ortho and para positions, with reference to the hydroxy substituent. Examples of such compounds are 2-phenylphenol, 3-phenylphenol, 4-phenylphenol, ortho, meta, or para cresols, 2,6-dimethylphenol, 2,2'-dihydroxydiphenol, 2,6-dimethoxyphenol, and 3,5-dimethoxyphenol. For specificity to ozone, the unsubstituted phenylphenols are preferred. For maximized sensitivity and selectivity, 2-phenylphenol is believed to be the most desirable reagent, and this compound is available commercially as are the other hydroxyphenol compounds previously referred to.

For preparing the detector system, the MBTH ketone azine and the hydroxyphenyl compound are dissolved in an organic solvent in which they are mutually soluble and which is inert with respect to the reagents. For example, acetone or methylethylketone may be used as a solvent. The solution concentration is selected as a matter of convenience but is not critical. In general, relatively concentrated solutions are preferred to reduce the amount of solvent to be evaporated, but the concentration should be such that both reagents are fully dissolved.

The reagent system of this invention is sensitive to ozone and/or to ozone and nitrogen dioxide over a wide variety of proportions of the MBTH ketone azine to the hydroxyphenyl compound. For example, the reagents may be used in molar proportions within the range from one mole of the ketone azine to 1 to 10 moles of the hydroxyphenyl compound. A preferred range is from 1 mole of the ketone azine per 3 to 7 moles of the hydroxyphenyl compound. For most uses, an optimized sensitivity is obtainable at a molar ratio of 1:4 to 1:6 ketone azine to hydroxyphenyl compound.

In practicing the present invention, a solution is formed of the two reagents as described above and that solution is applied to an inert solid support which may be a porous absorbent support or a non-porous support. When the support is porous, the solution can impregnate the support. When it is non-porous, a solution is applied to one or more surfaces of the substrate to form a liquid layer thereon. In either case, after application of the solution, a solvent is evaporated leaving the reagents in the form of a solid phase mixture either impregnated in the porous support or as a coating on a non-porous support. The supports may be in the form of sheets, strips, or granules. For example, filter papers formed from cellulose fibers or glass fibers can be used as well as woven cloth formed from cotton or synthetic fibers. Granular absorbents which may be used include silica gel, alumina, and zeolites. Preferably, the support should be readily wettable by the applied solution.

After the detector has been prepared as described, it is ready for use in the qualitative or quantitative detection of ozone and/or hydrogen dioxide. In preferred embodiments, as described above, the reagent system is specific to ozone and does not produce a color reaction with nitrogen dioxide. Where quantitative readings are desired, the detector may be calibrated in addition to color intensity and color chips or a color chip provided to assist in interpreting the quantity of ozone detected. It will be appreciated by those skilled in the colorimetric arts that this reagent system is particularly suitable for use in passive monitoring devices utilizing visual comparison standards. It is also suitable for elution in a suitable solvent, such as acetone, and the intensity of the color determined spectrophotometrically.

The method of this invention and the results obtainable thereby are further illustrated by the following examples.

EXAMPLE I

Preparation of Detector

All reagents were the purest commercially available grade and deionized water was used throughout the preparation. The synthesis was a modification of the Hunig and Fritsch method for the preparation of MBTH-formaldehyde condensation product (*Liebigs, Ann. Chem.*, 1957, 609, 172). 3-Methyl-2-benzothiazolinone hydrazone hydrochloride (Aldrich), 4.0 g, was dissolved in 200 mL of water with stirring and the free base precipitated by the addition of 10 mL of concentrated ammonium hydroxide solution. The crystalline product was filtered with suction and washed until the wash water no longer tested alkaline with pH indicator paper. The solid product was then vacuum dried at room temperature, and dissovled with vigorous shaking in 100 mL of absolute ethanol in a 250 mL round-bottom flask. To this solution, 20 mL of acetone and 10 mL of glacial acetic acid were added, and the solution refluxed over a boiling water bath for 0.5 h. After cooling to room temperature; the slow addition of 300 mL of water produced a white product which, upon filtering and drying at room temperature, was obtained in nearly theoretical yield as 3-methyl-2-benzothiazolinone acetone azine. The product was sufficiently pure for use but it may be further purified by recrystallization for cyclohexanol.

Whatman No. 1 filter paper circles, 4.25 cu diameter, were soaked for 20 m in 50.0 mL of an acetone solution containing 1.10 g of 3-methyl-1-benzothiazolinone acetone azine (0.005 mole) and 3.40 g of 2-phenylphenol (0.02 mole), drained of excess solution to near dryness, dried for 20 minutes on a clean glass plate, and stored in a sealed container.

TESTING OF DETECTOR

Reflectance Spectrophotometer

The term reflection absorbance can be used for measurements made with a Perkin-Elmer Model 124 visible-ultraviolet spectrophotometer modified for reflectance measurements on reagents supported on filter paper. The reflectance attachment used was similar to the micro specular reflectance attachment described by Wendlandt and Hecht "Reflectance Spectroscopy", Interscience: New York, 1966, p. 124. The incident beam in this instrument was deflected onto a sample surface and back again to the same path to the photomultiplier tube. Loss of incident radiant energy at 535 nm was read as absorbance in the regular manner.

Exposure Vessel

As inverted Kimble low form, cap-style 50 mm inside diameter weighting bottle was modified by sealing 5 mm inside diameter tubing through the bottom. In the vessel used in this study, the inlet tube was bent to direct the flow of ozone onto the center of the enclosed reagent paper for convenience of reflectance measurement instead of to the side as previously constructed. Insofar as possible, all tubing that carried reactive gas mixtures was borosilicate glass or poly(tetrafluoroethylene) tubing. Glass-to-glass connections were made with inert seals with O-rings.

Ozone Generator

A McMillan Model 1000 ozone generator (Columbia Scientific Industries Corp., Austin, Tex.) was calibrated iodimetrically by the method of Flamm, *Environ. Sci. Technol.*. 1977, 11, 978.

Interference Tests

The tests for interference with nitrogen dioxide were done at the ppm level in an air dilution system using permeation tubes. The tests for reactivity with sulfur dioxide, bromine, iodine vapor and chlorine were qualitative.

RESULTS AND DISCUSSION

Nonlinear response curves similar to those previously obtained with supported solid reagents were obtained when reflection absorbance values at 535 nm (a) were plotted against a fixed ozone concentration of 12.00 ppm at various exposure times from 0 to 600 seconds. The reflection absorbance increased in a smooth curve from about 0.05 to 0.3 values. Measurements were also made against a fixed exposure time of 500 s to various ozone concentrations from 0.2 to 1.0 ppm. The values for reflection absorbance increased in a smooth curve from 0.1 to 0.3. These reflection measurements demonstrated the reproducibility of the method for the intended use of the detector which would involve visual comparison to permanent color standards in passive monitoring devices for ozone in air.

The reagent papers were stable on storage and the color produced by ozone is stable to light. As water is not involved in the reaction, no humectant was required and relative humidity was not a factor in the color development.

A study of reagent reactivity vs. mole ration showed that a 1:5 or 1:6 mole ratio of MBTH acetone azine:2-phenylphenol were the most sensitive mixtures but the ratio was not highly critical. The faint pink tinge present in 2-phenylphenol was not involved in the reagent reaction with ozone.

Specificity for atmospheric ozone was determined on the basis of the interference test. No interference was observed with atmospheric oxygen, nitrogen dioxide, sulfur dioxide, bromine or iodine vapor, and only a light yellow color was produced by chlorine. On exposure to atmospheric ozone in the parts per million range, such as 0.2 to 1.0 ppm, a red-violet color was produced.

EXAMPLE II

Following the procedure of Example I, MBTH ketone azine reagents were prepared from cyclohexanone and phenyl cyclohexanone. When tested with 2-phenylphenol as a second reagent, the same red-violet color was produced on contact with low ppm concentrations of ozone but no color reaction was obtained with nitrogen dioxide.

EXAMPLE III

Following the procedure of Example I, 3-phenylphenol and 4-phenylphenol were substituted for the 2-phenylphenol. The resulting color detectors comprising a mixture of these compounds with MBTH acetone azine was found to be a specific colorimetric detector for low concentrations of ozone in the air, the detector combination not being reactive with hydrogen dioxide or other oxidizing agents in air. However, detectors containing the same molar proportions of 3-phenylphenol and 4-phenylphenol as 2-phenylphenol in Example I were not as sensitive to ozone.

EXAMPLE IV

Further experiments were conducted according to the procedures of Example I as follows: (a) 2,2'-Dihydroxydiphenol was substituted on an equal molar basis for the 2-phenylphenol, and found to produce blue-violet color on exposure to ozone. It was not reactive with nitrogen dioxide. (b) 2,6-Dimethoxyphenol was similarly substituted for 2-phenylphenol and found to be sensitive to ozone but not nitrogen dioxide, producing a red-orange color on exposure to the ozone. (c) 3,5-dimethoxyphenol was tested in admixture with MBTH acetone azine. Reactivity with ozone was confirmed, but the reactivity was not specific and a color change also being obtained with nitrogen dioxide. (d) Substitution of 1-napthol or 2-napthol for 2-phenyl-phenol produced a reagent which responded to both ozone and nitrogen dioxide.

We claim:

1. The method of preparing a colorimetric detector for ozone, comprising:
    (a) forming a solution of a 3-methyl-2-benzothiazolinone (MBTH) ketone azine and a hydroxyphenyl compound in an inert organic solvent, said hydroxyphenyl compound containing at least one phenyl group with a hydroxy substituent which is unsubstituted in the ortho, or para, or both the ortho and para positions with reference to the hydroxy substituent;
    (b) applying said solution to an inert solid support; and
    (c) evaporating the solvent from the applied solution to form a solid phase mixture on said support of said MBTH ketone azine and said hydroxyphenyl compound for use as said colorimetric detector.

2. The method of claim 1 in which said solid support is formed of a porous absorbent material and said solid phase mixture is dispersed therein.

3. The method of claim 1 in which said solid support is non-porous and said solid phase mixture forms a coating thereon.

4. The colorimetric detector prepared by the method of claims 1, 2, or 3.

5. The method of claim 1 in which said MBTH ketone azine is MBTH acetone azine.

6. The method of claim 1 in which said hydroxyphenyl compound is 2-phenylphenol.

7. The method for preparing a colorimetric detector for ozone which does not react with nitrogen dioxide, comprising:
    (a) forming a solution of 3-methyl-2-benzathiazolinone (MBTH) acetone azine and 2-phenylphenol;
    (b) applying said solution to an inert solid support; and
    (c) evaporating the solvent from the applied solution to form a solid phase mixture on said support, said MBTH acetone azine and said 2-phenylphenol for use as a colorimetric detector.

8. The method of claim 7 in which said solid support is formed of a porous absorbent material and said solid phase mixture is dispersed therein.

9. The method of claim 7 in which said solid support is non-porous and said solid phase mixture forms a coating thereon.

10. The colorimetric detector prepared by the process of claims 7, 8, or 9.

11. The method of claim 1 or claim 7 in which said applied solution contains from about 1 mole of the MBTH ketone azine per 3 to 7 moles of the hydroxyphenyl compound.

12. The colormetric detector prepared by the method of claim 11.

* * * * *